United States Patent
Kricheldorf et al.

(10) Patent No.: US 6,297,350 B1
(45) Date of Patent: Oct. 2, 2001

(54) PROCESS FOR THE PREPARATION OF COPOLYESTERS

(75) Inventors: Hans R. Kricheldorf, Hamburg; Ingrid Kreiser-Saunders, Bremen; Dirk-Olaf Damrau, Leverlcusen, all of (DE)

(73) Assignee: Ferring GmbH, Kiel (DE)

( * ) Notice: Subject to any disclaimer, the term of this patent is extended or adjusted under 35 U.S.C. 154(b) by 0 days.

(21) Appl. No.: 09/424,935

(22) PCT Filed: May 25, 1998

(86) PCT No.: PCT/EP98/03141

§ 371 Date: Feb. 15, 2000

§ 102(e) Date: Feb. 15, 2000

(87) PCT Pub. No.: WO98/55531

PCT Pub. Date: Dec. 10, 1998

(30) Foreign Application Priority Data

Jun. 6, 1997 (DE) .............................. 197 23 807

(51) Int. Cl.[7] .............................. C08G 63/08; C08K 3/10
(52) U.S. Cl. .................... 528/354; 528/357; 528/358; 528/361; 528/403; 528/409; 528/410; 524/779; 524/783; 524/785; 524/788
(58) Field of Search .................. 528/354, 357, 528/358, 361, 403, 409, 410; 524/779, 783, 785, 788

(56) References Cited

U.S. PATENT DOCUMENTS

| | | | |
|---|---|---|---|
| 5,051,272 | * | 9/1991 | Hermes et al. ..................... 427/2 |
| 5,319,107 | * | 6/1994 | Benecke et al. ................... 549/274 |
| 5,543,494 | | 8/1996 | Perego et al. . |
| 5,760,118 | * | 6/1998 | Sinclair et al. .................... 524/306 |
| 5,795,584 | * | 8/1988 | Totakura et al. .................. 424/426 |
| 5,844,068 | * | 12/1998 | Otera et al. ...................... 528/361 |

FOREIGN PATENT DOCUMENTS 09095606    4/1997 (JP) .

OTHER PUBLICATIONS

*Polymer*, vol. 20, Dec. 1979: "Biodegradable polymers for use in surgery–polyglycolic/poly(actic acid) homo– and copolymers:1", pp. 1459–1464.
Kricheldorf et al Macromol. Chem. Phys. 198, 1753–1766 (1997) Polylactones, 37[a)] Polymerization of L–lactide initiated with Zn(II) L–lactate and other resorbable Zn salts.
Kricheldorf et al Macromol. Chem. Phys. 198, 1767–1774 (1997) Polylactones, 38[a)] Polymerization of L–lactide with Fe(II) lactate and other resorbable (FEII) salts.
Kricheldorf et al Macromol. (1984) 17(10), 2173–2181 Polylactones, Copolymerization of Glycolide and ipsilon-–Caprolalctone.
Ajioka et al Bull. Chem. Soc. Jpn. (1995), 68(8), 2125–31 Basic Properties of polylactic acid produced etc.
Schwach et al. Polym. Bull. Berlin (1996). 37(6), 771–776 Zn lactate as initiator of DL–lactate ring opening etc.
PL–56799 CA–Abstr. AN:1969:423363.

* cited by examiner

Primary Examiner—Samuel A. Acquah
(74) Attorney, Agent, or Firm—Nixon & Vanderhye

(57) ABSTRACT

Copolyesters are prepared using cyclic esters or carbonates as monomers and a metallic salt of the formula $Me^{2+}X_2$ as catalyst. $Me^{2+}$ represents Ca, Fe(II), Mg, Mn(II) or Zn, and X is an anion of an aminocarboxylic acid, hydroxycarboxylic acid or a halide. Monomer and catalyst are used in a monomer/catalyst ratio of greater than 100.

22 Claims, No Drawings

PROCESS FOR THE PREPARATION OF COPOLYESTERS

The invention relates to a process for the preparation of copolyesters using cyclic esters as monomers and a metallic salt of the formula $Me^{2+}X_2$ as catalyst.

Biologically degradable plastics such as polylactides or copolyesters of lactic acid with other hydroxycarboxylic acids are used to an increasing extent for medical and pharmaceutical purposes, for example as matrix materials for pharmaceutical active ingredients, as medical suture materials, as devices for setting bone fractures or as wound materials.

Amorphous polymers are generally preferred in the preparation of depot medicaments, since they exhibit a homogeneous degradation behaviour in the body and therefore ensure a uniform release of the active ingredient. Moreover, active ingredients can form deposits better in amorphous than in crystalline polymer regions.

Since homopolymers mostly have a semicrystalline structure, copolymers are preferred for the preparation of depot medicaments.

Gilding and Reed, Polymer 20 (1979) 1459, describe the preparation of copolyesters of glycolic and lactic acid using tin octoate as initiator. Tin octoate, however, allows only insufficient control of the polymerization reaction. Initially, the glycolide predominantly incorporated into the growing polymer chains due to the different reactivities of the monomers. Only when this is largely used up does a noteworthy incorporation of the lactide take place. As a consequence, block copolymers are obtained which tend to form crystalline regions. Moreover, the use of tin salts and other heavy metal salts in the preparation of polymers for medical purposes is problematical.

Kricheldorf et al., Makromol. Chem., Suppl. 12, 25–38 (1985) 25, investigate the copolymerization of glycolide with L,L-lactide and other lactones. In addition to tin salts, $FeCl_3$, $ZnCl_2$, ZnO, ZnS and zinc dust inter alia are used as initiators. Monomer and initiator are used in a ratio of 100:1. Here, too, only block copolymers were obtained when $FeCl_3$, $ZnCl_2$ and ZnS were used. Only ZnO and zinc dust resulted in amorphous copolymers at temperatures of 150° C., but ZnO brings about a racemization of L-lactide and produces only relatively low molecular weights. After polymerization, zinc powder must be laboriously separated off in an additional purification step, and the molecular weights of the polymers can scarcely be controlled.

Bero et al., Makromol. Chem. 194 (1993), 907, and Kasperczyk and Bero, Makromol. Chem. 194 (1993), 913, disclose the copolymerization of L,L-lactide and E-caprolactone using inter alia ZnEtOiPr as initiator and chlorobenzene as solvent. The use of non-toxic solvents or solvent-free reactions are not described.

None of the processes known up to now allows the reproducible, controlled preparation of copolyesters with a random sequence. Moreover, the use of the named initiators is in some cases associated with serious disadvantages.

The object of the present invention is to provide a process which allows the reproducible preparation of copolyesters with a random sequence under controlled conditions.

This object was surprisingly achieved by polymerizing cyclic esters in the presence of a metallic salt according to the formula $Me^{2+}X_2$, in which $Me^{2+}$ represents Mg, Ca, Fe(II), Mn(II) or Zn, and X is an anion of an aminocarboxylic acid, hydroxycarboxylic acid or a halide, and in which monomer and catalyst are used in a monomer/catalyst ratio of greater than 100.

Preferred aminocarboxylic acids are aliphatic or aromatic, α- or ω-aminocarboxylic acid such as 4-amino- and/or 4-(acetylamino)benzoic acid, saturated or unsaturated $C_1$–$C_{18}$ acylaminobenzoic acid, particularly preferably $C_2$–$C_{18}$ acylaminobenzoic acid with an even number of C atoms, in particular $C_4$, $C_6$, $C_{16}$ or $C_{18}$ acylaminobenzoic acid. Also preferred are α- and ω-aminoalkanoic acids, particularly α- and ω-amino-$C_2$–$C_6$-alkanoic acids or N-acyl, N-alkoxycarbonyl or oligopeptide derivatives thereof, acyl preferably having the meaning given above. Particularly suitable N-alkoxycarbonyl radicals are $C_1$–$C_{18}$, in particular $C_1$–$C_4$ alkoxycarbonyl radicals, most preferred is ethoxycarbonyl. Preferred oligopeptide derivatives are dipeptide derivatives, in particular dipeptide derivatives of the amino acids glycine, alanine, sarcosine and proline.

Preferred hydroxycarboxylic acids are aliphatic or aromatic α- or ω-hydroxycarboxylic acids such as glycolic acid, β-hydroxybutyric acid, β-hydroxyvaleric acid, lactic acid, mandelic acid, 4-hydroxybenzoic acid, salicylic acid and N-acetylsalicylic acid.

Preferred halides are chloride, bromide and iodide.

$Me^{2+}$ preferably represents Fe(II), Mn(II) or Zn, quite particularly preferably Zn.

X preferably represents lactate, mandelate, glycolate, bromide, iodide, particularly preferably lactate, bromide, quite particularly preferably lactate.

Particularly preferred catalysts are iron(II) lactate, manganese lactate, zinc lactate, zinc mandelate, zinc bromide and zinc iodide, in particular zinc bromide, zinc lactate and iron(II) lactate.

Two or more different monomers are used to prepare copolymers, preferably structurally different monomers being used, i.e. monomers which differ not only by virtue of their stereochemistry.

Suitable as monomers are in particular cyclic esters and cyclocarbonates. Preferred cyclic esters are dilactones, such as glycolide and lactides, as well as lactones and esters according to the formulae

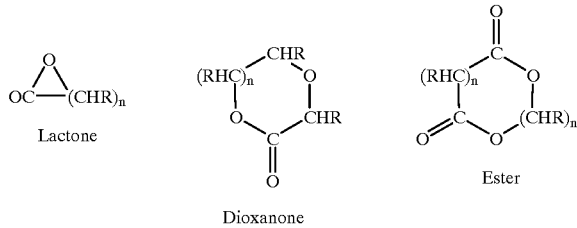

in which m=0 to 4, preferably 1 to 2 and quite particularly preferably 2. The index n represents 2 to 12, preferably 2 to 6 and particularly preferably 2 to 4, and R represents H, $CH_3$ or $C_2H_5$.

Preferred lactides are L,L-lactide and the racemate of L,L-lactide and D,D-lactide. L,L-lactide is often also called L-lactide.

Lactones are inner esters of the hydroxycarboxylic acids. Preferred lactones are β-butyrolactone, ε-caprolactone, p-dioxanone and (L- or D,L)-δ-valerolactone. Quite particularly preferred are ε-caprolactone and p-dioxanone.

Preferred cyclocarbonates are compounds according to the formula

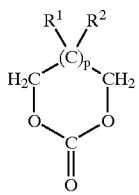

in which p=1 to 8, preferably 1 or 2. $R^1$ and $R^2$ independently of one another represent H, straight-chain $C_1$–$C_6$ alkyl or form, together with the carbon atom to which they are bound, a 5- or 6-membered Spiro ring.

Two different cyclic esters, in particular two different lactones and/or dilactones, or cyclocarbonates or a mixture of at least one cyclic ester and at least one cyclocarbonate are preferably reacted with one another.

Mixtures of lactide and glycolide, lactide and ε-caprolactone as well as lactide and trimethylene carbonate are preferred. Lactide and glycolide are preferably used in a molar ratio of 1:1 to 9:1, lactide and ε-caprolactone or lactide and trimethylene carbonate in a ratio of 9:1 to 1:9, in particular 9:1 to 1:1.

The polymerization is carried out primarily as a bulk polymerization, i.e. in the melt in the absence of solvents. Small amounts of an inert liquid such as e.g. paraffin oil or a siloxane, for example polydimethylsiloxane, can be added in order to improve heat transfer. The process according to the invention is preferably carried out in the absence of water.

The initiators can be used in the form of solutions in order to facilitate dosage. A preferred solvent is diethyl ether. Furthermore, it was found that, when ether solutions of the catalyst are used, polymers with higher molecular weights can be obtained. This process variant is particularly suitable when metal halides are used.

The polymerization temperature is preferably 40 to 250° C., particularly preferably 60 to 200° C. and quite particularly preferably 60 to 180° C. Most preferred is a temperature range from 100 to 160° C. The optimum reaction temperature for the system in question depends on the monomers used and on the catalyst used. For example in the case of mixtures of lactide and ε-caprolactone, a reaction temperature in the range from 100 to 150° C., in the case of mixtures of glycolide and lactide a temperature in the range from 130 to 160° C. and in the case of mixtures of cyclocarbonates and ε-caprolactone a temperature in the range from 60 to 120° C. is preferred.

The reaction time depends on the reaction temperature and on the composition of the reaction mixture and is usually between 2 hours and 2 weeks, preferably between 0.5 and 2 days.

Monomer and catalyst are preferably used in a monomer/catalyst molar ratio of >100 to 15,000, particularly preferably 150 to 4000.

The process according to the invention can be carried out in the presence of coinitiators. Suitable as coinitiators are in particular alcohols, preferably primary alcohols. The coinitiators are incorporated as a terminal group into the polyester chain. Biologically active polymers and oligomers can be obtained by using biologically active alcohols such as geraniol, menthol, hormones, e.g. stigmasterol, testosterone or cortisone, vitamins, e.g. α-tocopherol, and pharmaceutical active ingredients. Moreover, a control of the molecular weight of the polymers is possible via the ratio of monomer to coinitiator.

The process according to the invention allows the controlled and reproducible preparation of copolyesters with an approximately random sequence under mild conditions. For example, during the copolymerization of glycolide and lactide (molar ratio of glycolide to lactide 1:1), copolyesters are obtained with glycolide block lengths of less than 5, in particular less than 4 glycolic acid units.

Previously, the preparation of random copolyesters required either high temperatures which resulted in small molecular weights, or the use of toxic initiators or initiators disadvantageous for other reasons. The initiators used according to the invention contain exclusively ions which are found in the human or animal body. They are fully resorbable and biocompatible. The process is therefore particularly suitable for the preparation of biologically degradable, resorbable polyesters.

Biologically degradable polyesters are those which can be enzymatically or hydrolytically degraded at temperatures below ca. 50° C. to harmless, low-molecular compounds.

Resorbable polyesters are those which are degraded fully to non-toxic compounds in the animal or human body.

On account of the largely random distribution of the monomer components, the polymers prepared using the process according to the invention are practically completely amorphous and have no crystalline regions. They are characterized by a very uniform biological degradation and are suitable in particular for the preparation of medicaments with controlled release of the active ingredient such as, e.g., depot medicaments, as carriers and containers for cell cultures, for example for osteosynthesis, for the preparation of films, powders and foams for wound treatment, for example transparent dressings for burns.

For the preparation of depot medicaments, a polymer prepared according to the invention is loaded with the desired active ingredient, for example by coprecipitating the dissolved or suspended active ingredient with the polymer from a polymer solution, by co-freeze-drying a solution of polymer and active ingredient or by kneading the active ingredient into the polymer. Suitable as active ingredients are, for example, steroid hormones, peptide hormones, contraceptives, antidepressants and antitumour reagents.

The release behaviour of the active ingredients can be varied within broad ranges by varying the composition and the molecular weight of the polymer.

High active ingredient/polymer ratios can be achieved on account of the amorphous character of the polymers. Moreover, the amorphous structure guarantees a uniform degradation behaviour and thus ensures even release of the active ingredient.

Catalysts are preferably used for the polymerization with a purity of at least 97%, preferably 99% and particularly preferably >99%. Catalysts of this degree of purity can be obtained from commercial products by customary purification processes such as for example by recrystallization. A high purity of catalysts and monomers favours the formation of polymers with high molecular weights.

Particularly pure zinc lactate can be obtained by suspending zinc oxide and/or zinc carbonate together with lactide, preferably L,L-lactide, in water, then stirring the suspension until a clear solution is obtained and subsequently isolating the product. For the isolation, the water is for example evaporated until a cloudy solution forms, which is cooled. The precipitated product can be filtered off. The crude product can be purified further by recrystallization from water. This process produces zinc lactate of high purity and one of the remarkable features of this process is characterized by its simple handling.

Alternatively pure zinc lactate can be obtained by mixing ZnO, ethyl-L-lactate and water and heating the mixture until a clear solution is obtained. The zinc lactate formed can be isolated by concentrating the solution by removal of the solvent followed by cooling. The precipitated product is filtered off and can be purified further as described above.

The metallic salts according to the invention have a high storability and resistance to oxidation. Zinc lactate can be stored for practically unlimited periods. Moreover, the salts of the amino- and hydroxycarboxylic acids in particular are characterized by a very low hygroscopicity. The catalysts are therefore easy to handle and ensure high reproducibility of the process according to the invention.

The invention is explained in more detail below with reference to embodiments.

EXAMPLE 1

Preparation of Zinc Lactate from Ethyl Lactate

ZnO (25 mmol, ZnO purissimum, E. Merck Co., Darmstadt, FRG), ethyl-L-lactate (100 mmol, $[\alpha]^{20}_D=10°$, Aldrich Co., Milwaukee, Wis., USA) and water (100 ml) were mixed and stirred under reflux for 3 hours. The clear solution was concentrated in vacuo to ca. 50% of its initial volume and then cooled in an ice bath. The precipitated product was then filtered off, recrystallized twice from water (in each case 30 ml) and dried at 110° C. in vacuo over $P_4O_{10}$.

Yield: 36%.

| $[\alpha]^{20}_D$ −8.1°, c = 2.5 g/dl in $H_2O$. | | | | | |
|---|---|---|---|---|---|
| $C_6H_{10}O_6Zn$ (243.52 g/mol) | Calc.: | C | 29.59 | H | 4.14 |
| | Found: | C | 29.36 | H | 4.14 |

EXAMPLE 2

Preparation of Zinc Lactate from L-Lactide

L-lactide (S grade, Boehringer Ingelheim KG, Ingelheim, FRG) was recrystallized twice from ethyl acetate and dried over $P_4O_{10}$. ZnO (60 mmol, E. Merck Co., Darmstadt, FRG) and the dried L-lactide (80 mmol) were suspended in distilled water (150 ml) and stirred for 24 hours at 20 to 22° C. The clear solution was concentrated until clouding occurred, then cooled in an ice bath, and the precipitated product was filtered off. The untreated product was recrystallized from water (50 ml). Yield: 40%.

| $[\alpha]^{20}_D$ − 9.1°, c = 2.5 g/dl in $H_2O$ | | | | | |
|---|---|---|---|---|---|
| $C_6H_{10}O_6Zn$ (243.52 g/mol) | Calc.: | C | 29.59 | H | 4.14 |
| | Found: | C | 29.97 | H | 4.18 |

EXAMPLE 3

Preparation of zinc-L-mandelate $ZnCl_2$ (25 mmol, purity 99.9%, Aldrich Co., Milwaukee, Wis., USA) was dissolved in water (100 ml) and the solution was added dropwise with stirring to a solution of Li-L-mandelate (60 mmol, Aldrich Co., Milwaukee, Wis., USA) in water (100 ml). The precipitated product was filtered off, washed with cold water (1° C.) and recrystallized from water. Yield after drying at 110° C. in vacuo: 61%.

| $[\alpha]^{20}_D$ + 92.5°, c = 0.1 g/dl in $H_2O$ | | | | | |
|---|---|---|---|---|---|
| $C_{16}H_{14}O_6Zn$ (367.7) | Calc.: | C | 52.27 | H | 3.84 |
| | Found: | C | 51.85 | H | 3.86 |

EXAMPLE 4

Preparation of iron(II)-L-lactate

A solution of Li-L-lactate (50 mmol, Sigma Chemicals, Munich, FRG) in oxygen-free methanol (50 ml) and a solution of $FeCl_2$ (25 mmol) (Aldrich Co., Milwaukee, Wis., USA), also in oxygen-free methanol (50 ml), were mixed slowly with stirring, a white deposit forming. The deposit was filtered off, washed with cold methanol until chloride-free and dried in vacuo at 60° C. Yield: 47%.

| $[\alpha]^{20}_D$ + 12.88°, c = 2.5 g/dl in $H_2O$ | | | | | |
|---|---|---|---|---|---|
| $C_6H_{10}O_6Fe$ (236.0) | Calc.: | C | 30.80 | H | 4.31 |
| | Found: | C | 30.86 | H | 4.45 |

EXAMPLE 5

Copolymerization of glycolide and L,L-lactide using zinc lactate as catalyst

Recrystallized glycolide, L-lactide (Aldrich Co., Milwaukee, Wis., USA) and catalyst were weighed in the proportions given in Table 1 under nitrogen into a 50 ml Erlenmeyer flask with silanized glass walls. The reaction vessel was closed with a glass stopper which was secured with a steel clip, and fully immersed in a temperature-controlled oil bath having a temperature of 150° C. After 48 hrs, the flask was removed from the oil bath, cooled, the reaction product was dissolved in dichloromethane (50 ml) and precipitated by pouring this solution into cold methanol (700 ml). The isolated copolyester was dried in vacuo at 50° C.

TABLE 1

ZnLac$_2$-catalysed bulk copolymerization of glycolide and L,L-lactide at 150° C. with a reaction time of 48 hours

| Ex. | Molar ratio lactide/glycolide | monomer[a]/ catalyst | Yield [%] | Composition[b] lactide/ glycolide [%] | $\eta$inh[c]/ dl/g |
|---|---|---|---|---|---|
| 5.1 | 9/1 | 1000/1 | 92 | 89/11 | 0.70 |
| 5.2 | 8/2 | 1000/1 | 87 | 79/21 | 0.43 |
| 5.3 | 7/3 | 1000/1 | 92 | 70/30 | 0.54 |
| 5.4 | 6/4 | 1000/1 | 90 | 57/43 | 0.49 |
| 5.5 | 5/5 | 1000/1 | 89 | 48/52 | 0.70 |

[a]molar sum of both monomers
[b]determined by means of the $^1$H-NMR spectra
[c]measured at 25° C. with c = 2 g/l in $CH_2Cl_2$/trifluoroacetic acid (volume ratio 4:1)

The composition of the copolyesters was determined by means of their $^1$H-NMR spectra by computer-aided quantification of the signal intensities. The $^1$H-NMR spectra were measured at 25° C. using a Bruker AC-100 or AM-360 FT spectrometer in 5 mm o.d. sample tubes.

The inherent viscosities were determined using an automatic Ubbelohde viscometer (Viscoboy, Lauda) thermostatically controlled at 25° C.

Optical rotations were measured in a polarimeter (Perkin Elmer Md 421) at 25° C. in 10 cm-long vessels.

EXAMPLE 6

Copolymerization of glycolide and L,L-lactide using zinc lactate as catalyst Glycolide (0.5 mol) and L-lactide (0.5 mol) (both S-grade, Boehringer Ingelheim KG, Ingelheim) were heated to 150° C. in a 250 ml three-necked flask with silanized glass walls, equipped with a stirrer, in order to obtain a homogeneous melt of both monomers. The initiator was then added, the reaction vessel was closed with glass stoppers and secured with steel clips. The stirrer was removed after the mixture had become too viscous to be stirred. The third flask neck was also closed with a glass stopper and secured with a steel clip. The flask was cooled after the reaction times given in Table 2, 10 g of the reaction product were dissolved in dichloromethane/trifluoroacetic acid (volume ratio 4:1), precipitated in cold methanol, and the product was filtered off. The isolated copolyester was dried in vacuo at 40° C.

The average block lengths of the glycolide ($L_G$) and lactide ($L_L$) units were then determined by means of their $^{13}$C-NMR spectra. To this end, the intensities of the CO signals were measured and evaluated according to the following equations:

$$L_G = \frac{I_{GG}}{I_{GL}} + 1 = \frac{I_{GG}}{I_{LG}} + 1$$

$$L_L = \frac{I_{LL}}{I_{GL}} + 1 = \frac{I_{LL}}{I_{CL}} + 1$$

$I_{GG}$ and $I_{LL}$ are the signal intensities of CO signals which indicate the linkage of glycolide units with glycolide units and lactide units with lactide units.

$I_{GL}$ and $I_{LG}$ are the intensities of the CO signals which indicate glycolide-lactide and lactide-glycolide linkages (diads).

The results are summarized in Table 2.

TABLE 2

ZnLac$_2$-catalysed bulk copolymerization of glycolide and L,L-lactide (molar ratio 1:1) at 150° C.

| Ex. | Monomer[a]/ Catalyst | Reaction time [hr] | Yield [%] | ηinh[b]/ dl/g | Average block length[c] | |
|---|---|---|---|---|---|---|
| | | | | | $L_G$ | $L_L$ |
| 6.1 | 500/1 | 24 | 93 | 0.55 | 3.0 | 3.1 |
| 6.2 | 500/1 | 48 | 91 | 0.47 | 2.7 | 2.8 |
| 6.3 | 1000/1 | 48 | 89 | 0.70 | 2.9 | 3.1 |
| 6.4 | 1000/1 | 72 | 95 | 0.62 | 2.7 | 2.7 |
| 6.5 | 4000/1 | 48 | 85 | 0.62 | 3.7 | 3.5 |
| 6.6 | 4000/1 | 72 | 93 | 0.43 | 3.8 | 3.5 |

[a]molar sum of both monomers
[b]measured at 25° C. with c = 2 g/l in CH$_2$Cl$_2$/trifluoroacetic acid (volume ratio 4:1)
[c]determined by means of the $^{13}$C-NMR Spectra

EXAMPLE 7

Copolymerization of L,L-lactide and ε-caprolactone using zinc lactate as catalyst Inanalogy to Example 5, L,L-lactide and ε-caprolactone were copolymerized in a molar ratio of 1:2 at 120° C. and 150° C. The results are summarized in Table 3.

TABLE 3

ZnLac$_2$-catalysed bulk copolymerization of L,L-lactide and ε-caprolactone (molar ratio 1:2)

| Ex. | Monomer[a]/ Catalyst | Temp. (° C.) | Time [hrs] | Yield [%] | Composition[b] lactide/ caprolactone [%] | ηinh[c]/ dl/g |
|---|---|---|---|---|---|---|
| 7.1 | 1000/1 | 120 | 48 | 67 | 60/40 | 0.61 |
| 7.2 | 1000/1 | 150 | 48 | 90 | 49/51 | 0.75 |
| 7.3 | 1000/1 | 120 | 96 | 88 | 51/49 | 0.99 |
| 7.4 | 1000/1 | 150 | 96 | 90 | 49/51 | 0.80 |
| 7.5 | 1000/1 | 120 | 192 | 96 | 50/50 | 0.96 |

[a]molar sum of both monomers
[b]determined by means of the $^1$H-NMR spectra
[c]measured at 25° C. with c = 2 g/l in CH$_2$Cl$_2$

EXAMPLE 8

Copolymerization of ε-caprolactone and trimethylene carbonate using zinc lactate as catalyst 5.7 g (0.05 mol) ε-caprolactone (distilled twice over CaH$_2$) and 5.1 g (0.05 mol) trimethylene carbonate (Boehringer Ingelheim, recrystallized from ethyl acetate and dried in vacuo over phorphorus pentoxide) were weighed into a 100 ml Erlenmeyer flask silanized with dimethyldichlorosilane. The flask was closed with a glass stopper and immersed in an oil bath temperature-controlled at 100° C. and 150° C. respectively. After the monomers had melted, 0.0353 g Zn(lac)$_2$ were added as initiator (monomer/ initiator=1000). The flask was again closed and left in the oil bath for the times mentioned in Table 4. The product was then dissolved in 100 ml dichloromethane, precipitated from ca. 1 l cold methanol and stored in the freezer for 30 minutes. After the methanol had been decanted off, the product was dried in vacuo at room temperature. The results are summarized in Table 4.

Inanalogy to Example 6, the average block lengths of the ε-caprolactone units ($L_C$) and trimethylene carbonate units ($L_T$) were determined. The following values were found: $L_C$=2; $L_T$=2.

TABLE 4

ZnLac$_2$-initiated bulk copolymerization of ε-caprolactone and trimethylene carbonate (TMC) (1:1)

| Ex. | Monomer[a]/ Initiator | Temp. [° C.] | Time [hrs] | Yield [%] | Composition[b] caprolactone/ TMC [%] | ηinh[c]/ dl/g |
|---|---|---|---|---|---|---|
| 8.1 | 1000/1 | 100 | 8 | — | — | — |
| 8.2 | 1000/1 | 100 | 24 | 2 | — | — |
| 8.3 | 1000/1 | 100 | 48 | 87 | 49/51 | 0.80 |
| 8.4 | 1000/1 | 150 | 8 | 97 | 51/49 | 0.815 |
| 8.5 | 1000/1 | 150 | 24 | 97 | 48.5/51.5 | 1.01 |
| 8.6 | 1000/1 | 150 | 48 | 95 | 52/48 | 0.83 |

[a]molar sum of both monomers
[b]determined by means of the $^1$H-NMR spectra
[c]measured at 25° C. with c = 2 g/l in CH$_2$Cl$_2$

EXAMPLE 9

Copolymerization of β-D,L-butyrolactone and trimethylene carbonate using zinc lactate as catalyst 4.3 g (0.05 mol) β-D,L-butyrolactone (Aldrich) and 5.1 g (0.05 mol) trimethylene carbonate (Boehringer Ingelheim, recrystallized from ethyl acetate and dried in vacuo over phorphorus pentoxide) were weighed into a 100 ml Erlenmeyer flask silanized with dimethyldichlorosilane. The Erlenmeyer flask was closed with a glass stopper and immersed in an oil bath temperature-controlled at 100° C. After the monomers had melted, 0.0353 g of Zn(lac)$_2$ were added as initiator (monomer/initiator=1000). The flask was again closed and left in the temperature-controlled oil bath for 8 to 72 hours. The product was then dissolved in 100 ml dichloromethane, precipitated from ca. 1 l cold methanol and stored in the freezer for 30 minutes. After the solvent had been decanted off, the product was dried in vacuo at room temperature. The results are summarized in Table 5.

TABLE 5

ZnLac$_2$-initiated copolymerization of β-D,L-butyrolactone and trimethylene carbonate (TMC) (1:1)

| Ex. | Monomer[a]/ Initiator | Temp. [° C.] | Time [hrs] | Yield [%] | Composition[b] butyrolactone/ TMC [%] | ηinh[c]/ dl/g |
|---|---|---|---|---|---|---|
| 9.1 | 1000/1 | 100 | 8 | 6 | 24/76 | — |
| 9.2 | 1000/1 | 100 | 24 | 32 | 32.5/67.5 | 0.19 |
| 9.3 | 1000/1 | 100 | 72 | 18 | 38/62 | 0.19 |

[a] molar sum of both monomers
[b] determined by means of the $^1$H-NMR spectra
[c] measured at 25° C. with c = 2 g/l in CH$_2$Cl$_2$

EXAMPLE 10

Copolymerization of L,L-lactide and trimethylene carbonate using zinc lactate as catalyst 4.8 g (0.033 mol) L,L-lactide (Boehringer Ingelheim) and 6.8 g (0.066 mol) trimethylene carbonate (Boehringer Ingelheim) were weighed into a 100 ml Erlenmeyer flask silanized with dimethyldichlorosilane. Both monomers had been recrystallized beforehand from ethyl acetate and dried in vacuo over phosphorus pentoxide. The Erlenmeyer flask was closed with a glass stopper and immersed in an oil bath temperature-controlled at 100° C. and 150° C. respectively. After the monomers had melted, Zn(lac)$_2$ was added as initiator. The quantity of initiator was measured in such a way that the monomer/initiator ratios listed in Table 6 were attained (0.0176 g Zn(lac)$_2$ produce e.g. a monomer/initiator ratio of 2000). The flask was again closed and left in the temperature-controlled oil bath for 8 to 168 hours. The product was then dissolved in 100 ml dichloromethane, precipitated from ca. 1 l cold methanol and dried in vacuo at 40° C. The results are summarized in Table 6.

Analogously to Example 6, the average block lengths of the L-lactide units (L$_L$) and trimethylene carbonate units (L$_T$) were determined. The following values were found: L$_L$=1.8; L$_T$=2.7.

TABLE 6

Znlac$_2$-initiated bulk copolymerization of L,L-lactide and trimethylene carbonate (TMC) (1:2)

| Ex. | Monomer[a]/ Initiator | Temp. [° C.] | Time [hrs] | Yield [%] | Composition[b] lactide/TMC [%] | ηinh[c]/ dl/g |
|---|---|---|---|---|---|---|
| 10.1 | 500/1 | 100 | 24 | 19 | 67.5/32.5 | 0.26 |
| 10.2 | 500/1 | 100 | 48 | 71 | 57/43 | 0.32 |
| 10.3 | 500/1 | 100 | 96 | 85 | 44/56 | 0.375 |
| 10.4 | 2000/1 | 100 | 72 | 8 | 67.5/32.5 | 0.15 |

TABLE 6-continued

Znlac$_2$-initiated bulk copolymerization of L,L-lactide and trimethylene carbonate (TMC) (1:2)

| Ex. | Monomer[a]/ Initiator | Temp. [° C.] | Time [hrs] | Yield [%] | Composition[b] lactide/TMC [%] | ηinh[c]/ dl/g |
|---|---|---|---|---|---|---|
| 10.5 | 2000/1 | 100 | 96 | 24 | 57.5/42.5 | 0.24 |
| 10.6 | 2000/1 | 100 | 168 | 66 | 65/35 | 0.33 |
| 10.7 | 500/1 | 150 | 8 | 91 | 48.4/51.6 | 0.25 |
| 10.8 | 500/1 | 150 | 24 | 91 | 43.7/56.3 | 0.36 |
| 10.9 | 2000/1 | 150 | 24 | 90 | 51/49 | 0.38 |
| 10.10 | 2000/1 | 150 | 48 | 93 | 50.5/49.5 | 0.27 |

[a] molar sum of both monomers
[b] determined by means of the $^1$H-NMR spectra
[c] measured at 25° C. with c = 2 g/l in CH$_2$Cl$_2$

EXAMPLE 11

Copolymerization of glycolide and L,L-lactide using zinc lactate as catalyst and diethylene glycol monobutyl ether as coinitiator 129.6 g (0.9 mol) L,L-lactide (degree of purity S, Boehringer Ingelheim, Ingelheim, FRG) and 11.6 g (0.1 mol) glycolide (degree of purity S, Boehringer Ingelheim, Ingelheim, FRG) were weighed into a 250 ml three-necked flask silanized with dimethyldichlorosilane. Both monomers had been dried beforehand for 24 hours over phosphorus pentoxide in vacuo in a desiccator. The three-necked flask was provided with a glass stirrer and a jacket, the other necks were closed with glass stoppers and secured with steel springs.

The flask was then immersed in an oil bath temperature-controlled at 130° C. After the monomers had been melted with stirring, the flask was opened and, with further stirring, 0.707 g zinc lactate were added as catalyst (monomer/catalyst=500), and 4 ml of a 1 M solution of diethylene glycol monobutyl ether in dry dioxane were added as coinitiator (monomer/coinitiator=250). The mixture was again left in the oil bath. The glass stirrer was removed after the resulting copolymer had reached a viscosity which made further stirring impossible. The opening was likewise closed with a glass stopper and the reaction was continued. After 8 days the flask was removed from the oil bath and cooled.

The working-up of the polymerization mixture was carried out as described in Example 5. The analysis of the copolymer gave the following results: $\eta_{inh}$=0.49 dl/g; L$_L$=2; L$_G$=10; T$_g$=52° C. (determined by DSC measurement).

EXAMPLE 12

Polymerization of L-lactide using zinc lactate as catalyst and various biologically active alcohols as coinitiators Inanalogy to Example 11, L-lactide was polymerized at 150° C. using zinc lactate as catalyst. The biologically active alcohols listed in Table 7 were added as coinitiators. The low viscosities and the $^1$H-NMR spectra show that vitamins and hormones are integrated into the polymer as terminal ester groups.

TABLE 7

Bulk polymerization of L-lactide[a)] at 150° C. using ZnLac$_2$[b)] as catalyst and various alcohols as coinitiators

| Ex. | Coinitiator | Monomer/ Benzyl alcohol | Yield [%] | ηinh[c)] _-/ dl/g | Calculated degree of polymerization[d)] | Degree of polymerization[e)] $^1$H-NMR |
|---|---|---|---|---|---|---|
| 12.1 | Testosterone | 10 | 55 | 0.09 | 19 | 42 |
| 12.2 | Tocopherol | 10 | 51 | 0.12 | 19 | 31 |
| 12.3 | Stigmasterol | 10 | 48 | 0.09 | 19 | 43 |
| 12.4 | Testosterone | 25 | 83 | 0.17 | 48 | 75 |
| 12.5 | Tocopherol | 25 | 80 | 0.22 | 48 | 60 |
| 12.6 | Stigmasterol | 25 | 79 | 0.18 | 48 | 80 |

[a)]Recrystallized once from ethyl acetate
[b)]monomer/catalyst ratio 4000:1
[c)]measured at 20° C. with c = 2 g/l in CH$_2$Cl$_2$
[d)]calculated as degree of polymerization = monomer/coinitiator molar ratio, assuming a 95% conversion according to the equation: Degree of polymerization = mol monomer/mol coinitiator · % conversion/100
[e)]experimental values of $^1$H-NMR terminal group analysis

EXAMPLE 13

Copolymerization of glycolide and L,L-lactide using zinc lactate as catalyst

Inanalogy to Example 5, a mixture of glycolide (degree of purity S, Boehringer Ingelheim, Ingelheim, FRG) and L,L-lactide (degree. of purity S, Boehringer Ingelheim, Ingelheim, FRG) was polymerized at 150° C. using zinc lactate as catalyst. In each case 0.4 mol of the monomers was used (molar ratio 1:1). Reaction conditions and results are summarized in Table 8.

TABLE 8

ZnLac$_2$-initiated bulk copolymerization of glycolide and L,L-lactide (molar ratio 1:1) at 150° C.)

| Ex. | Monomer[a)]/ Catalyst | Time [hr] | Yield [%] | ηinh[b)]/ dl/g | Average block length[c)] | |
|---|---|---|---|---|---|---|
| | | | | | $L_G$ | $L_L$ |
| 13.1 | 500/1 | 24 | 93 | 0.55 | 3.0 | 3.1 |
| 13.2 | 500/1 | 48 | 91 | 0.47 | 2.7 | 2.8 |
| 13.3 | 1000/1 | 48 | 89 | 0.70 | 2.9 | 3.1 |
| 13.4 | 1000/1 | 72 | 95 | 0.62 | 2.7 | 2.7 |
| 13.5 | 4000/1 | 48 | 85 | 0.62 | 3.7 | 3.5 |
| 13.6 | 4000/1 | 72 | 93 | 0.43 | 3.8 | 3.5 |

[a)]molar sum of both monomers
[b)]measured at 25° C. with c = 2 g/l in CH$_2$Cl$_2$/trifluoroacetic acid (volume ratio 4:1)
[c)]determined analogously to Example 6 by means of the $^{13}$C-NMR spectra

EXAMPLE 14

Copolymerization of glycolide and L,L-lactide using zinc bromide as catalyst 72 g (0.5 mol) L,L-lactide (degree of purity S, Boehringer Ingelheim, Ingelheim, FRG) and 58 g (0.5 mol) glycolide (degree of purity S, Boehringer Ingelheim, Ingelheim, FRG) were weighed into a 250 ml three-necked flask silanized with dimethyldichlorosilane. Both monomers had been dried beforehand for 24 hours over phosphorus pentoxide in vacuo in a desiccator. The three-necked flask was provided with a glass stirrer and a jacket, the other necks were closed with glass stoppers and secured with steel springs. The flask was then immersed in an oil bath temperature-controlled at 150° C. After the monomers had been melted with stirring, the flask was opened and, with further stirring, 2 ml of a 1 M ZnBr$_2$ solution in dry diethyl ether were added as catalyst (monomer/catalyst=500), and 4 ml of a 1 M solution of diethylene glycol monobutyl ether in dry dioxane were added as coinitiator (monomer/coinitiator=250). The mixture was again left in the oil bath. The glass stirrer was removed after the resulting copolymer had reached a viscosity which made further stirring impossible. The opening was likewise closed with a glass stopper and the reaction was continued. After 96 hours the flask was removed from the oil bath and cooled. The working-up of the polymerization mixture was carried out as described in Example 5. The analysis of the copolymer gave the following results: $\eta_{inh}$=0.4 dl/g; $L_L$=2.3; $L_G$=2.2; $T_g$=42° C.

EXAMPLE 15

Copolymerization of L-lactide and glycolide using manganese(II) salts as initiators Glycolide (12.5 mmol, recrystallized 1× from ethyl acetate), L-lactide (37.5 mmol, recrystallized 1× from ethyl acetate) and Mn(II) salt (0.1 mol) were weighed into a 50 ml Erlenmeyer flask with silanized glass walls. The flask was closed with a glass stopper and immersed in an oil bath thermostatically controlled at 150° C. After the monomers had melted, they were tossed for ca. 5 minutes in the oil bath in order to achieve thorough mixing. The flask was then left in the oil bath for 2 to 3 days and then the reaction product was dissolved in 50 ml dichloromethane, precipitated in 600 ml cold methanol and dried in vacuo at 40° C. The results for different Mn(II) salts are summarized in Table 9.

TABLE 9

Bulk copolymerization of L-lactide and glycolide (3:1) at 150° C.

| Ex. | Initiator | Monomer/ Catalyst | Time [hrs] | Yield[a)] [%] | ηinh[b)] [dl/g] |
|---|---|---|---|---|---|
| 15.1 | MnCl$_2$ | 500/1 | 48 | 40 | 0.23 |
| 15.2 | | 500/1 | 72 | 49 | 0.22 |
| 15.3 | | 2000/1 | 48 | 37 | 0.22 |
| 15.4 | | 2000/1 | 72 | 42 | 0.22 |
| 15.5 | MnBr$_2$ | 500/1 | 48 | 82 | 0.32 |
| 15.6 | | 500/1 | 72 | 89 | 0.24 |
| 15.7 | | 2000/1 | 48 | 55 | 0.24 |
| 15.8 | | 2000/1 | 72 | 54 | 0.20 |
| 15.9 | MnI$_2$ | 500/1 | 48 | 83 | 0.25 |
| 15.10 | | 500/1 | 72 | 85 | 0.24 |
| 15.11 | | 2000/1 | 48 | 11 | — |
| 15.12 | | 2000/1 | 72 | 26 | 0.16 |
| 15.13 | Mn acetate | 500/1 | 48 | 84 | 0.25 |
| 15.14 | | 500/1 | 72 | 89 | 0.25 |
| 15.15 | | 2000/1 | 48 | 55 | 0.24 |
| 15.16 | | 2000/1 | 72 | 67 | 0.21 |
| 15.17[c)] | Mn lactate | 500/1 | 48 | 81 | 0.29 |
| 15.18 | | 500/1 | 72 | 90 | 0.30 |
| 15.19 | | 2000/1 | 48 | 43 | 0.27 |
| 15.20 | | 2000/1 | 72 | 48 | 0.22 |

[a)]after precipitation in methanol
[b)]measured at 25° C. with c = 2 g/l in CH$_2$Cl$_2$ (1:4)
[c)]ratio of L-lactide/glycolide = 3.1:1 (determined by $^1$H-NMR spectroscopy)

EXAMPLE 16

Copolymerization of L-lactide and glycolide using iron(II) salts as initiators

Glycolide (12.5 mmol, recrystallized 1× from ethyl acetate), L-lactide (37.5 mmol, recrystallized 1× from ethyl acetate) and Fe(II) lactate or FeCl$_2$ were weighed into a 50 ml Erlenmeyer flask with silanized glass walls, the flask was closed with a glass stopper and immersed in an oil bath thermostatically controlled at 150° C. After the monomers had melted, the flask was tossed in the oil bath for ca. 5 minutes in order to achieve thorough mixing. After a reaction time of 2 to 4 days, the reaction product was dissolved in 50 ml dichloromethane, precipitated in 600 ml cold methanol and dried in vacuo at 40° C. The results are summarized in Table 10.

TABLE 10

Bulk copolymerization of L-lactide and glycolide (3:1) at 150° C.

| Ex. | Initiator | Monomer/Catalyst | Time [hrs] | Yield[a] [%] | $\eta_{inh}$[b] [dl/g] |
|---|---|---|---|---|---|
| 16.1 | Fe lactate | 500/1 | 48 | 74 | 0.27 |
| 16.2 | | 500/1 | 72 | 77 | 0.33 |
| 16.3[c] | | 2000/1 | 48 | 71 | 0.33 |
| 16.4 | | 2000/1 | 72 | 74 | 0.34 |
| 16.5 | FeCl$_2$ | 500/1 | 48 | 77 | 0.31 |
| 16.6 | | 500/1 | 72 | 82 | 0.31 |
| 16.7 | | 2000/1 | 48 | 65 | 0.23 |
| 16.8 | | 2000/1 | 72 | 72 | 0.28 |

[a] after precipitation in methanol
[b] measured at 25° C. with c = 2 g/l in TFA/CH$_2$Cl$_2$ (1:4)
[c] ratio of L-lactide/glycolide 2.9:1 (determined by $^1$H-NMR spectroscopy)

EXAMPLE 17

Copolymerization of L-lactide and caprolactone using zinc salts as initiators

Caprolactone (33.3 mmol, 1× distilled), L-lactide (16.7 mmol, recrystallized 1× from ethyl acetate) and Zn(II) salicylate or Zn(II) prolinate (zinc salt of the amino acid proline) were weighed into a 50 ml Erlenmeyer flask with silanized glass walls, the flask was closed with a glass stopper and immersed in an oil bath thermostatically controlled at 1500C. After the lactide had melted, the flask was tossed in the oil bath for ca. 5 minutes in order to achieve thorough mixing. After a reaction time of 2 to 4 days, the reaction product was dissolved in 50 ml dichloromethane, precipitated in 600 ml cold methanol and dried in vacuo at 40° C. The results are shown in Table 11.

TABLE 11

Bulk copolymerization of L-lactide and caprolactone (1:2) at 150° C.

| Ex. | Initiator | Monomer/Catalyst | Time [hrs] | Yield[a] [%] | $\eta_{inh}$[b] [dl/g] |
|---|---|---|---|---|---|
| 17.1 | Zn salicylate | 500/1 | 48 | 88 | 0.38 |
| 17.2 | | 500/1 | 96 | 58 | 0.44 |
| 17.3 | | 2000/1 | 48 | 86 | 0.29 |
| 17.4[c] | | 2000/1 | 96 | 91 | 0.42 |
| 17.5 | Zn prolinate | 500/1 | 48 | 64 | 0.24 |
| 17.6 | | 500/1 | 96 | 82 | 0.29 |
| 17.7 | | 2000/1 | 48 | 68 | 0.25 |
| 17.8 | | 2000/1 | 96 | 76 | 0.37 |

[a] after precipitation in methanol
[b] measured at 25° C. with c = 2 g/l in CH$_2$Cl$_2$
[c] ratio of ε-oxycaproyl/lactyl units 1.1:1; length of ε-oxycaproyl blocks: L$_c$ = 3.24

EXAMPLE 18

Copolymerization of L-lactide and caprolactone using manganese(II) salts as initiators Inanalogy to Example 17, a mixture of caprolactone (33.3 mmol) and L-lactide (16.7 mmol) was copolymerized using MnBr$_2$ or Mn lactate at 150° C. The reaction conditions and results are summarized in Table 12.

TABLE 12

Bulk copolymerization of L-lactide and caprolactone (1:2) at 150° C.

| Ex. | Initiator | Monomer/Catalyst | Time [hrs] | Yield[a] [%] | $\eta_{inh}$[b] [dl/g] |
|---|---|---|---|---|---|
| 18.1 | MnBr$_2$ | 500/1 | 48 | 66 | 0.30 |
| 18.2 | | 500/1 | 96 | 72 | 0.33 |
| 18.3 | | 2000/1 | 48 | 16 | 0.32 |
| 18.4 | | 2000/1 | 96 | 34 | 0.32 |
| 18.5 | Mn lactate | 500/1 | 48 | 77 | 0.27 |
| 18.6 | | 500/1 | 96 | 79 | 0.32 |
| 18.7 | | 2000/1 | 48 | 23 | 0.33 |
| 18.8 | | 2000/1 | 96 | 48 | 0.39 |

[a] after precipitation in methanol
[b] measured at 25° C. with c = 2 g/l in CH$_2$Cl$_2$

What is claimed is:

1. A process for the preparation of copolyesters using cyclic esters or cyclocarbonates or a mixture of at least one cyclic ester and at least one cyclocarbonate as monomers and a metallic salt of the formula Me$^{2+}$X$_2$ as catalyst, wherein Me$^{2+}$ represents Ca, Fe(II), Mg, Mn(II) or Zn, and X is an anion of an aminocarboxylic acid, hydroxycarboxylic acid, bromide or iodide, that monomer and catalyst are used in a monomer/catalyst molar ratio of greater than 100, and the monomers are structurally different.

2. A process according to claim 1, wherein Me$^{2+}$ represents Fe(II), Mn(II) or Zn.

3. A process according to claim 1, wherein said aminocarboxylic acid is 4-amino- or 4-(acetylamino)benzoic acid, a saturated or unsaturated C$_1$–C$_{18}$ acylaminobenzoic acid, an α- and ω-amino-C$_2$–C$_6$-alkanoic acid, or a N-acyl, N-alkoxycarbonyl or oligopeptide derivative thereof.

4. A process according to claim 1, wherein X is mandelate, glycolate, iodide, bromide or lactate.

5. A process according to claim 1, wherein iron lactate, manganese lactate or zinc lactate is used as catalyst.

6. A process according to claim 1, wherein at least two different cyclic esters or cyclocarbonates or a mixture of at least one cyclic ester and at least one cyclocarbonate is used as monomers.

7. A process according to claim 6, wherein a glycolide, a lactide, a lactone of the formula

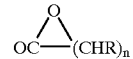

a dioxanone of the formula

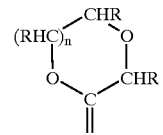

and/or an ester of the formula

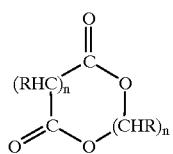

is used as cyclic ester, in which n=1–12 and R represents H, CH$_3$ and C$_2$H$_5$.

8. A process according to claim 6, wherein a cyclocarbonate of the formula

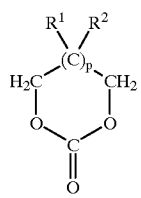

is used as monomer, in which p=1–8, and R$^1$ and R$^2$ independently of one another represent H or straight-chain C$_1$–C$_{16}$ alkyl or, together with the carbon atom to which they are bound, form a 5- or 6-membered spiro ring.

9. A process according to claim 6, wherein β-butyrolactone, ε-caprolactone, p-dioxanone and/or (L- or D, L)-δ-valerolactone is/are used as lactone.

10. A process according to claim 1, wherein the polymerization is carried out in the melt in the absence of solvents.

11. A process according to claim 1, wherein the polymerization is carried out at a temperature of 40 to 250° C.

12. A process according to claim 1, wherein monomer and catalyst are used in a monomer/catalyst molar ratio of 150 to 15,000.

13. A process according to claim 1, wherein, in addition, an alcohol is used as coinitiator.

14. A process according to claim 13, wherein a vitamin, hormone and/or a pharmaceutical active ingredient is/are used as coinitiator.

15. A process for the preparation of a medicament with controlled release of an active ingredient, comprising loading the polymer prepared according to claim 1 with a pharmaceutical active ingredient.

16. A process according to claim 15, wherein said active ingredient is dissolved or suspended in a polymer solution and then coprecipitated jointly with the polymer.

17. A copolyester produced by the process of claim 1.

18. A medicament providing controlled release of an active ingredient, the medicament comprising an active ingredient incorporated in the copolymer produced by the process of claim 1.

19. A process according to claim 1, wherein said hydroxycarboxylic acid is glycolic acid, β-hydroxybutyric acid, β-hydroxyvaleric acid, lactic acid, mandelic acid, 4-hydroxybenzoic acid, salicylic acid, or N-acetylsalicylic acid.

20. A process according to claim 1, wherein X is bromide or iodide.

21. A process according to claim 15, wherein said active ingredient and said polymer are dissolved in a solvent followed by freeze drying of this solution.

22. A process according to claim 15 wherein said active ingredient is kneaded into said polymer.

* * * * *